United States Patent
Merade et al.

(10) Patent No.: US 8,029,435 B2
(45) Date of Patent: *Oct. 4, 2011

(54) IMPLANTABLE SLING FOR THE TREATMENT OF INCONTINENCE AND METHOD OF USING THE SAME

(75) Inventors: Bryon L. Merade, Thousand Oaks, CA (US); Craig Comiter, Tucson, AZ (US); Victor Nitti, Wyckoff, NJ (US); Raymond Rackley, Shaker Heights, OH (US); Eugene Rhee, San Diego, CA (US); Sandip Vasavada, Westlake, OH (US); Kapri Ellenson, Los Alamitos, CA (US)

(73) Assignee: Coloplast A/S, Humlebaek (DK)

( * ) Notice: Subject to any disclaimer, the term of this patent is extended or adjusted under 35 U.S.C. 154(b) by 50 days.

This patent is subject to a terminal disclaimer.

(21) Appl. No.: 12/480,701

(22) Filed: Jun. 9, 2009

(65) Prior Publication Data
US 2009/0247816 A1    Oct. 1, 2009

Related U.S. Application Data

(63) Continuation of application No. 11/674,962, filed on Feb. 14, 2007, now Pat. No. 7,559,885.

(60) Provisional application No. 60/773,565, filed on Feb. 14, 2006.

(51) Int. Cl.
*A61F 2/02*    (2006.01)

(52) U.S. Cl. .................................................. 600/30
(58) Field of Classification Search ............. 600/29–32; 128/897–898, DIG. 25; 606/151
See application file for complete search history.

(56) References Cited

U.S. PATENT DOCUMENTS
7,559,885 B2 *    7/2009    Merade et al. .............. 600/30

OTHER PUBLICATIONS

Moir, The Journal of Obstetrics and Gyneacology, Jan. 1968.
Shaw, British Medical Journal, Jun. 1949.
Ulmsten et al, International Urogynecology Journal, vol. 7, 1996.

* cited by examiner

*Primary Examiner* — John Lacyk
(74) *Attorney, Agent, or Firm* — Coloplast Corp., Coloplast A/S; Daniel G. Chapik; Nicholas R. Baumann

(57) ABSTRACT

An implantable sling for the treatment of male or female incontinence and method of implementing the same. The sling comprises a urethral support portion and at least one anchoring portion extending therefrom. The anchoring portion is operatively positioned through the obturator foramen and about at least one ramus portion of the pelvis such that the support portion of the implant is operatively positioned at or distal to the bulbar urethra (male) or mid-urethral region (female) to treat urinary incontinence. In a preferred embodiment, the implant will have first and second anchoring portions extending from the support portion with each respective one of said anchoring portions being operative to be secured about dedicated ones of the patient's pubic ramus. The implants may further be fabricated from tissues, synthetic materials or combinations thereof.

9 Claims, 12 Drawing Sheets

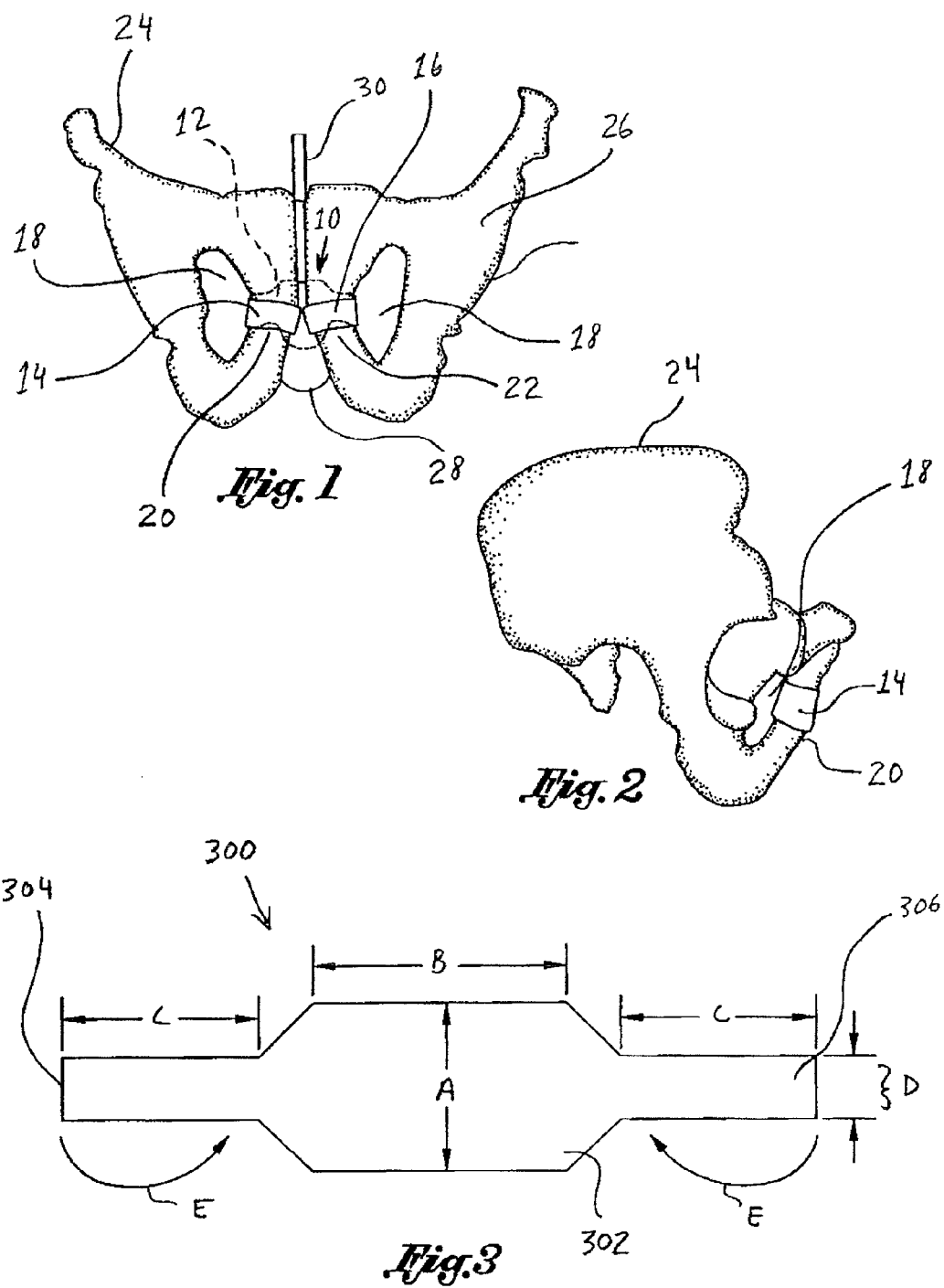

Stewart Crypt Hook

US 8,029,435 B2

IMPLANTABLE SLING FOR THE TREATMENT OF INCONTINENCE AND METHOD OF USING THE SAME

CROSS-REFERENCE TO RELATED APPLICATIONS

This application claims the benefit of and is a continuation of prior application Ser. No. 11/674,962, filed on Feb. 14, 2007, now U.S. Pat. No. 7,559,885 which claimed the benefit of the filing date of U.S. Provisional Application No. 60/773,565, filed on Feb. 14, 2006, both applications of which are incorporated by reference into this application in their entirety.

BACKGROUND OF THE INVENTION

The present invention is directed to surgical implants for the treatment of male or female incontinence, and in particular, implantable slings that are operative to provide sling-type support at or distal to the bulbar urethral region (male) or midurethral region (female) of a patient and operatively anchored into position via fixation about the patient's descending rami.

Of the estimated 19 million North American adults who have urinary incontinence, 20% are estimated to be men. Such condition can range in severity from partial to complete loss of bladder control and patients afflicted with urinary incontinence can experience varying degrees of urine loss. In addition, it is known that urinary incontinence may change over time and that men and women with light incontinence, for example, may experience minimal leakage during the occurrence of a provocative event, such as laughing or coughing, whereas men and women with heavy incontinence may experience continuous urine leakage.

Generally, urinary incontinence is not considered a disease, but rather a symptom or side effect of another medical condition. Among the causes known to cause male urinary incontinence include prostate surgery, and in particular total prostatectomy, head and spinal cord injury, infection, certain toxins, such as too much alcohol consumption, certain medications, such as sedating medications, and certain diseases, such as cancer, Parkinson's disease and multiple sclerosis. Indeed, male incontinence can be caused simply by virtue of the aging process or emotional distress. Female incontinence is caused by weakened and (or) stretched pelvic muscles, which is associated with childbirth, pregnancy, trauma, prior surgical procedures, and estrogen loss.

Each case of incontinence, however, is unique and no two people are affected by incontinence in the same way. There are, however, well-recognized types of incontinence and various ways to treat the same. Stress incontinence, which is the most common type of incontinence, wherein urine leakage occurs during the occurrence of a provocative event, such as sneezing, laughing, lifting heavy objects, or when the patient engages in any type of exercise that puts pressure on the bladder. Urge incontinence occurs when the patient wants to urinate but is incapable of exercising restraint until reaching a restroom. Additional types of incontinence include overflow incontinence, which occurs when the quantity of urine exceeds the capacity of the patient's bladder, and functional incontinence, which occurs when the patient has knowledge of the need to urinate but simply cannot access a restroom quickly enough due to a physical obstruction or debilitation.

To treat urinary incontinence, several options are available. Among the more effective types of recognized treatment include behavioral techniques, such as biofeedback, bladder training, and pelvic muscle exercises, and modifications of the patient's diet and fluid intake. With respect to the latter, it is known that eliminating or cutting back on certain types of substances, such as caffeine and alcohol, can help alleviate incontinence. There are additionally medications available, such as dicyclomine (Bentyl), flavoxate (Urispas), hyoscyamine sulfate (Anaspaz), imipramine (Tofranil), oxybutynin (Ditropan), tolterodine (Detrol), and propantheline (Pro-Banthine), phenylpropanolamine (Dexatrim), and pseudoephedrine (Sudafed) that are helpful in controlling urinary incontinence.

Surgery may additionally be an option to treat male and female urinary incontinence. Along these lines, surgical implants for males, such as the In-Vance, produced by American Medical Systems, Inc., of Minneapolis, Minn., is a commercially available surgical implant that is operative to provide structural support to the urethra for the treatment of stress incontinence. In this regard, the implant is operative to provide structural support to the urethra such that during a provocative event, the implant will provide structural support to the urethra thus causing the urine to be retained within the bladder and not leak through the urethra. Likewise, surgical implants for females, such as the In-Fast Ultra, produced by American Medical Systems, Inc. of Minneapolis, Minn. is a commercially available surgical implant that is operative to provide structural support to the urethra for the treatment of stress incontinence.

Utilizing sling implants to treat incontinence, however, has been known to have numerous drawbacks. Securing suburethral sling implants into position typically requires the use of bone screws, which are well-known in the art to be difficult and time consuming to deploy, and can result in significant patient discomfort, especially within the first couple of weeks following the surgical implantation.

In addition, implanting suburethral slings are often times difficult to secure into position with the optimal degree of tension. Indeed, the implantation of suburethral slings for the treatment of incontinence is well-recognized as complex, time consuming and can produce suboptimal clinical outcomes. Moreover, it is well recognized among surgeons that perform such implant procedures that sutures attached to bone anchors and/or sutures attached to bone screws utilized to secure the sling into position frequently break and that often times additional bone anchors or screws must be secured into position. In fact, each suture attached to bone anchors and or bone screws must typically be retensioned two to three times before optimal sling positioning and structural support to the urethra is achieved.

Accordingly, there is a substantial need in the art for a suburethral sling implant for the treatment of incontinence that is substantially easier to surgically secure into position and that can further provide an optimal degree of urethral support to thus effectively treat urinary incontinence. There is additionally a need in the art for an implant that is of simple construction, easy to surgically manipulate, and can be manufactured at relative low cost utilizing known implant materials, whether it be synthetic materials, natural tissues, or combinations thereof. There is yet a further need in the art for such an implant that can be secured into position such that the implant defines a suburethral sling portion operatively positioned at or distal to the bulbar urethra of the patient (male) or mid-urethral region (female) that remains anchored into position via the use of an anchoring portion that extends through the obturator foramen and remain secured at or near the descending rami of the patient's pelvis without the use of bone anchors. With respect to the latter, it would be exceptionally advantageous for such a surgical implant that could be anchored to the pubis through the obturator foramen preferably via the descending rami thereof.

BRIEF SUMMARY

The present invention specifically addresses and alleviates the above identified deficiencies in the art. In this regard, the present invention is directed to suburethral sling implants and methods of deploying the same that are effective and substantially easier to deploy than prior art implants and implantation techniques for treating incontinence. The implant comprises the combination of a urethral support portion and at least one anchoring portion. The support portion is operatively positioned at or distal to the bulbar urethra (male) or mid-urethral region (female). Per conventional suburethral slings, the support portion is operative to provide structural support to the urethra such that during the occurrence of a provocative event, the sling is operative to compressively engage the urethra to prevent urine leaking therefrom. The support portion will have a surface area that is at least 2 cm long by 1 cm wide to 8 cm long by 8 cm wide. Along these lines, it should be understood that the specific dimensions provided herein can vary by 50% or substantially greater, and retain its ability for use as an implant.

The anchor portion extends from the support portion. The anchor portion, which may take a variety of configurations, is operative to extend through the obturator foramen of the patient and become secured at a locus preferably at or near the descending ramus. To effectuate such attachment, it is contemplated that one or more sutures or other suitable means for attachment may be utilized to ensure that the anchor portion becomes secured about the ramus and that the support portion remains operatively positioned at or distal to the bulbar urethra (male) or mid-urethral region (female). In a preferred embodiment, the implant will have at least two anchor portions extending from the support portion with each respective anchor portion extending through the obturator foramen and attachable about respective ones of the patient's rami. The anchor portions will have a width ranging from between 0.5-4 cm and the length ranging from at least 5.0 cm to 45.0 cm. Along these lines, it should be understood that the specific dimensions provided herein can vary by 50% or substantially greater, and retain its ability for use as an implant. To the extent necessary, both the support and anchor portions of the implant may be surgically fashioned as necessary to optimize sizing and configuration of the implant to suit the needs of a specific patient.

In certain embodiments of the implant of the present invention, the same may take the form of implants having a central support structure with anchoring portions extending therefrom in opposed directions or may be fashioned to have generally "H", inverted "U", or "X" shapes. The implants may further be provided as generally rectangular, square or trapezoidal shapes and may further be provided with one or more apertures to accommodate the attachment of sutures, surgical tacks and the like. The implants of the present invention may further be fabricated such that sutures are pre-attached thereto, per the teachings of Applicants' coowned pending U.S. patent application Ser. No. 10/947,182, entitled READILY IMPLANTABLE SLING, filed Sep. 22, 2004, the teachings of which are expressly incorporated by reference. The implants of the present invention may further be fabricated from any of a variety of surgically compatible materials well-known in the art, including synthetic materials, such as synthetic mesh and the like, as well as natural materials, such as harvested tissues from sources such as animals, cadavers or the patient himself. The implants may further be fabricated such that the same are formed from combinations of materials, including but not limited to combinations of different types of synthetic materials, combinations of different types of natural tissues and/or combinations of both synthetic and natural tissues.

Regardless of the embodiment, in all procedures involving the implantation of the implants of the present invention, such procedures are performed with the patient assuming a lithotomy position. A vertical perineal (male) or vaginal (female) incision is made in the midline dissecting to expose the bulbar urethra (male) or urethra (female) and the inferior aspect of the descending rami bilaterally. A surgical introducer is utilized to introduce the implant into position, typically through the obturator foramen, in a manner that is substantially easier and less traumatic than conventional surgical procedures utilized to access and implant slings for the treatment of male or female incontinence. Once the surgical site is accessed, the anchoring portion will preferably be positioned through the obturator foramen and anchored into position. Surgical sutures and the like may be deployed to facilitate anchoring of the anchor portions of the implant. Minor variations wellknown to those skilled in the art may necessarily be made to effectuate optimal attachment and positioning of the support portion of the implant, as may be necessary for a given patient. In all cases, however, the surgical procedures and implants of the present invention provide a radically more efficient, effective and less traumatic surgical approach to the treatment of male or female incontinence.

BRIEF DESCRIPTION OF THE DRAWINGS

These and other features and advantages of the various embodiments disclosed herein will be better understood with respect to the following description and drawings, in which like numbers refer to like parts throughout.

FIG. 1 is a frontal perspective view of a pelvis, a bladder and a urethra extending therefrom with a sling-type implant shown operatively secured into position, the implant having a support portion aligned at or distal to the bulbar urethra and anchoring portions, the latter shown extending through the obturator foramen and secured about dedicated ones of the rami of each hip bone.

FIG. 2 is a side elevational view of the pelvis and implant of FIG. 1 showing a respective one of the anchor portions of the implant secured about the ramus.

FIG. 3 is a front elevational view of an implant for the treatment of male or female urinary incontinence as constructed in accordance with the present invention.

DETAILED DESCRIPTION

Figure 4:
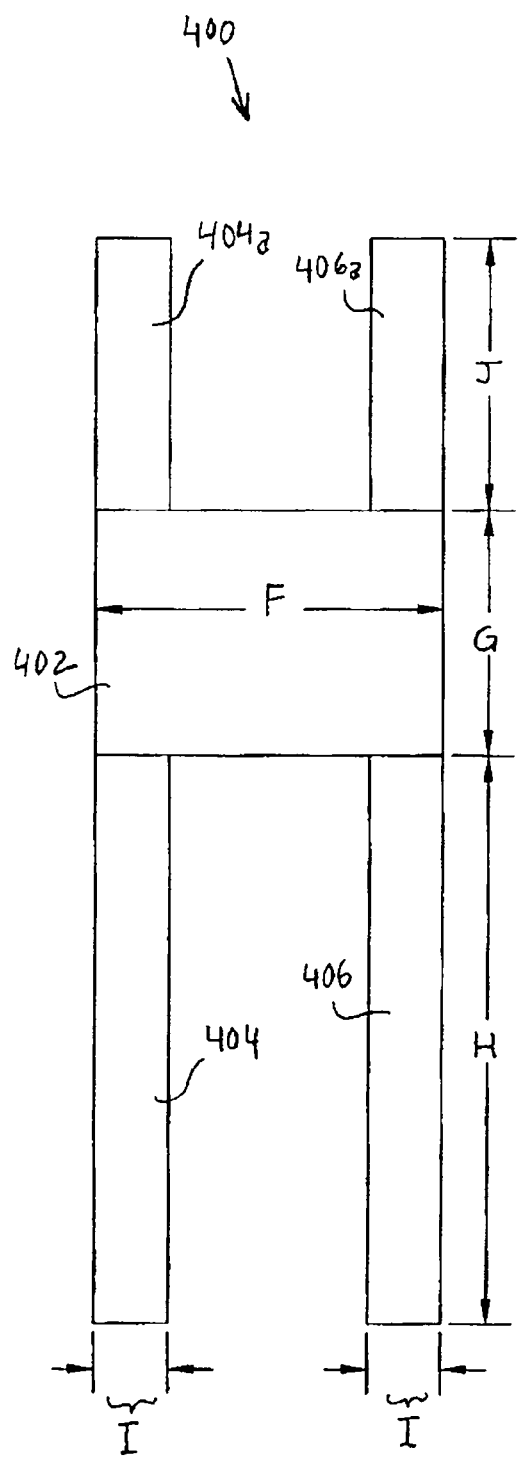
FIG. 4 is a front elevational view of an implant for the treatment of male urinary incontinence as constructed in accordance with another embodiment of the present invention.

Referring now to the drawings, initially to FIG. 1, there is shown an implant 10 for the treatment of male and female incontinence that is operative to provide suburethral support to thus prevent the leakage of urine, particularly when the patient experiences a provocative event. In this respect, the implant 10 is operative to act as a suburethral sling, as is known in the art, but is advantageously operative to be more easily secured into position than prior art sling implants. The implants of the present invention are further capable of being deployed in a manner that is far less traumatic than prior art sling implants and methods of surgically implanting the same, and further utilizing a novel attachment approach that provides for optimal suburethral positioning of the sling 10 in an exceptionally secure manner without the use of bone anchors.

In its broadest sense, the implants of the present invention comprise the combination of a urethral support portion and at least one anchoring portion. The support portion is operatively positioned at or distal to the bulbar urethra 28 (male) or mid-urethral region (female). The anchoring portion is operative to secure the support portion into position to thus provide structural support to the urethra, and particularly so during the occurrence of a provocative event. To achieve that end, the anchoring member is generally operative to extend through the obturator foramen and become secured at least one and preferably both of the patient's rami. In preferred embodiments of the invention, discussed more fully below, the anchor portion will be operatively interconnectable with the descending ramus of one of the patient's pelvis. Advantageously, the positioning of the anchor portion against the descending ramus will be accomplished without the use of bone screws, which are well-known in the art to be problematic to deploy and utilized as an attachment point for sutures and the like.

The implants of the present invention further may take a variety of embodiments. In certain of the embodiments depicted, the implant will include first and second attachment portions extending from the support portion with each attachment portion being operatively extensible through the obturator foramen and attachable to respective ones of the patient's descending rami. Such attachment portions may be operative to extend in opposed directions from the support portion or, alternatively, extend in generally parallel relation to one another from the support portion. In certain other embodiments, the support portion anchoring portion may be formed as a continuous segment or otherwise formed to have a generally rectangular or trapezoidal shape. Moreover, in certain embodiments, the implants of the present invention may incorporate the use of sutures or with other types of surgically implantable structures and the like to facilitate attachment of the same into position. Specifically, it is contemplated that such embodiments may rely upon a combination of structures in combination with certain portions of the implant to facilitate attachment and positioning thereof.

For purposes of defining the general parameters of implants of the present invention, it is presently believed that the support portion of the implant will define a surface area ranging from a 1 cm width by 2 cm length to an 8 cm width by 8.0 cm length. With respect to the anchor portion, the same will preferably define a surface area defined by a 0.5 cm width by 5.0 cm length to an area defined by a 4.0 cm width to a 45.0 cm length. With respect to the latter, it should further be understood that certain embodiments of the present invention, discussed more fully below, sutures may be utilized in operative combination with the anchoring portion or, in certain embodiments, exclusively with the support portion, to thus define means for attaching and securing the implant into position. In addition, it should be understood that the specific dimensions provided herein for both the support and anchor portions can vary by 50% or substantially greater, and retain their ability for use as an implant.

With respect to the fabrication of the implants of the present invention, the same may be made from either synthetic materials, such as surgical mesh and the like, natural tissues, such as tissues harvested from either an animal, cadaverous source or the patient himself, and/or combinations of synthetic and natural materials. Along these lines, it is contemplated that the implants of the present invention can be fabricated consistent with those methods disclosed in Applicant's co-owned and co-pending U.S. patent application Ser. No. 10/684,861, the teachings of which are expressly incorporated herein by reference. Along these lines, it is further contemplated that in certain embodiments of the present invention, the implants may be prefabricated with slings or sutures attached thereto, consistent with the teachings of Applicants' co-owned pending U.S. patent application Ser.

No. 10/947,182, entitled READILY IMPLANTABLE SLING, the teachings of which are likewise incorporated by reference.

Bearing the foregoing principles in mind, a detailed explanation is provided here below with respect to the structure, properties and functioning of the implants of the present invention. Referring again to FIG. 1, the implant 10 is situated such that the support portion 12 thereof is operatively positioned over the urethra. The implant 10 as depicted includes first and second support portions 14, 16 that are shown extending through the obturator foramen 18 and wrapped about dedicated ones of the descending rami 20, 22 of hip bones 24, 26, respectively.

FIG. 2 more clearly depicts such engagement between a respective one of the anchor portions 14 as extending through the obturator foramen 18 and engaged with descending ramus 20 of hip bone 24. In this regard, the implants 10 of the present invention generally, operate on the principle of including attachment of the implant into position via an anchoring mechanism that extends through the obturator foramen and becoming secured to at least one, and preferably both of the descending ramus of the patient; however, it should be understood that the descending ramus locus is not to limit the scope of the present invention and that attachment to any part of the periphery of the pubis and ischium may be considered suitable areas to which the implants of the present invention may be attached. Accordingly, fixation of the anchor portions at the descending rami or any other structure should not be deemed limiting in any respect.

Bearing the foregoing principles in mind, and referring now to remaining FIGS. 3-9, there are shown various embodiments of the implants of the present invention. Referring to FIG. 3, implant 300 is defined by support portion 302 with anchor portions 304, 306 extending in opposed directions therefrom. According to a preferred embodiment, the support portion will have a width "A" of approximately 4 cm and a length "B" of approximately 6 cm. Anchor portions 304, 306 may extend from support portion 302 via a tapered segment, as shown, and will have a length "C" of approximately 15 cm and a width "D" of approximately 2 cm. As discussed above, the implant 300 may be fabricated from either synthetic and/or natural materials. It should be understood, however, that the specific dimensions provided herein are not absolute, and variations in the length and width of both the support portion 302 and anchor portions 304, 306 can be readily made by those skilled in the art. Along these lines, it should be understood that the specific dimensions provided herein can vary by 50% or substantially greater, as discussed above, and retain its ability for use as an implant.

With respect to the procedure for implanting the implant 300 depicted in FIG. 3, Applicants believe that the best mode for performing the same will require the patient to assume a lithotomy position. A vertical perineal incision will be made in the midline dissecting to expose the bulbar urethra in the inferior aspect of the descending rami bilaterally. A suitable introducer is then passed from inside out or outside in through the upper aspect of the obturator foramen. A suture that is attached to a respective one of the anchor portions 304 or 306 is threaded through the introducer. The introducer is then retracted and the suture is pulled until a respective one of the ends of the anchor portion 304 or 306 to which the suture is attached can be grasped. The support portion 302 is then carried over the bulbar urethral complex and, thereafter, a second introducer is passed from inside or outside in on the contra-lateral side to thus enable the second other respective anchor portion extends through the obturator foramen. The second introducer is then retracted and a suture affixed to the respective other anchor portion extends around the pubic ramus. Once so positioned, tension is introduced to the implant 300 such that the support portion 302 thereof achieves optimal suburethral compression. The respective ends of anchor portions 304, 306 are then secured, preferably via attachment to support portion 302 at the edge of each pubic ramus. To achieve that end, it is contemplated that a suture with or without an additional tensioning disc (not shown) is passed through anchor portions 304, 306 to effectuate such attachment. Referring now to FIG. 4, there is shown a further embodiment 400 for use in the surgical treatment of male urinary incontinence. As depicted, the implant 400 includes a support portion 402 with first and second anchor portions 404, 406 depending therefrom in generally parallel relation to one another and additional anchor portions 404a, 406a, ascending therefrom to define an "H" shape. The implant 400, as depicted, is preferably formed such that support portion 402 has a width "F" of approximately 7 cm and a height "G" of approximately 5 cm. Anchor portions 404, 406 preferably have a length "H" of approximately 30 cm and a width "I" of 1 cm. Additional anchor portions 404a, 406a will have a width of approximately 1.5 cm and a height "J" of approximately 14 cm, and may preferably be formed as extensions of 404 and 406, respectively. Again, such dimensions can be varied as may be deemed appropriate by one skilled in the art. Specifically, it should be understood that the specific dimensions provided herein can vary by 50% or substantially greater, and retain its ability for use as an implant.

In the embodiment depicted, anchor portions 404, 406 are operative to extend through the retropubic space, from posterior to symphysis, or may extend via a transobturator route. Anchor portions 404a, 406a are operative to pass through the rectus fascia from anterior to symphysis.

In accordance with the best mode discussed above with respect to implant 300, the surgical procedure for implanting implant 400 will preferably be conducted with the patient assuming a lithotomy position whereby a vertical perineal incision will be made in the midline dissecting to expose the bulbar urethra in the descending pubic rami bilaterally. The bulbar spongiosis will be left intact. Thereafter, suprapubic transverse incisions of approximately 1 cm are made, 3 cm lateral to the midline on either side. A suitable introducer is then passed from such incisions and tunneled either superficially anterior to the pubic symphysis or retropubically and caused to exit through the initial perineal incision. A respective one of the ascending anchor portions 404a or 406a is attached to a suprapubic introducer 1700 and pulled through the suprapubic incisions. This same maneuver is then repeated for the respective other ascending anchor portion 404a or 406a. Alternatively, the ascending anchor portions 404a or 406a may be "lifted up" through the perineal incisions by attaching them to a transperineal introducer 1800 (FIG. 18) and tunneling the anchor portions either superficially anterior to the pubic symphysis or retropubically and causing them to exit along with the implant through the suprapubic incisions. The procedure using the transperineal introducer 1800 in this fashion also can be performed without first creating the suprapubic incisions. In other words, the transperineal introducer 1800 can itself be used to create an exit opening in the abdominal area at the time the anchor portions are being moved suprapubically.

Hereafter, two new incisions, which are preferably approximately 1 cm above the pubic symphysis are performed. The suitable introducer is then passed from above, retropubically, and out through the initial perineal incision. A respective one of the descending anchor portions 404 or 406 is then attached to the introducer and pulled up through such newly formed incision. Such procedure is repeated with respect to the other descending anchor portion 404 or 406, which as a consequence creates two sets of anchor portions, namely, descending anchor portions 404, 406 and ascending portions 404a, 406a in the suprapubic region. The ascending anchor portions 404a, 406a are then tunneled into the retropubic anchor portions 404, 406 beneath the skin and thereafter ascending portion 404a will be surgically connected with descending portion 404 and ascending portion 406a surgically attached to descending anchor portion 406. To achieve such surgical attachment, it is contemplated that such attachment may be attained via the use of sutures.

In a further refinement of such procedure, it is contemplated that surgical positioning of descending anchor portions 404, 406 can be accomplished via the use of a suitable introducer that is passed from outside in or inside out through the obturator foramen. A suture that is attached to the distal most end of respective one of anchor portions 404, 406 will be threaded to the introducer. Once the introducer is advanced through the obturator foramen, the same is retracted with the suture affixed to the end of descending anchor portion 404 or 406 is pulled until the end of the anchor portion 404 or 406 can be grasped. A second suitable introducer is utilized with respect to the surgical positioning of the respective other anchor portion 404 or 406 on the contra-lateral side. Once so positioned, anchor portions 404 and 406 can be affixed to ascending anchor portions 404a, 406a around the descending rami via the transobturator approach and secured on itself via a suture line.

Figure 5:
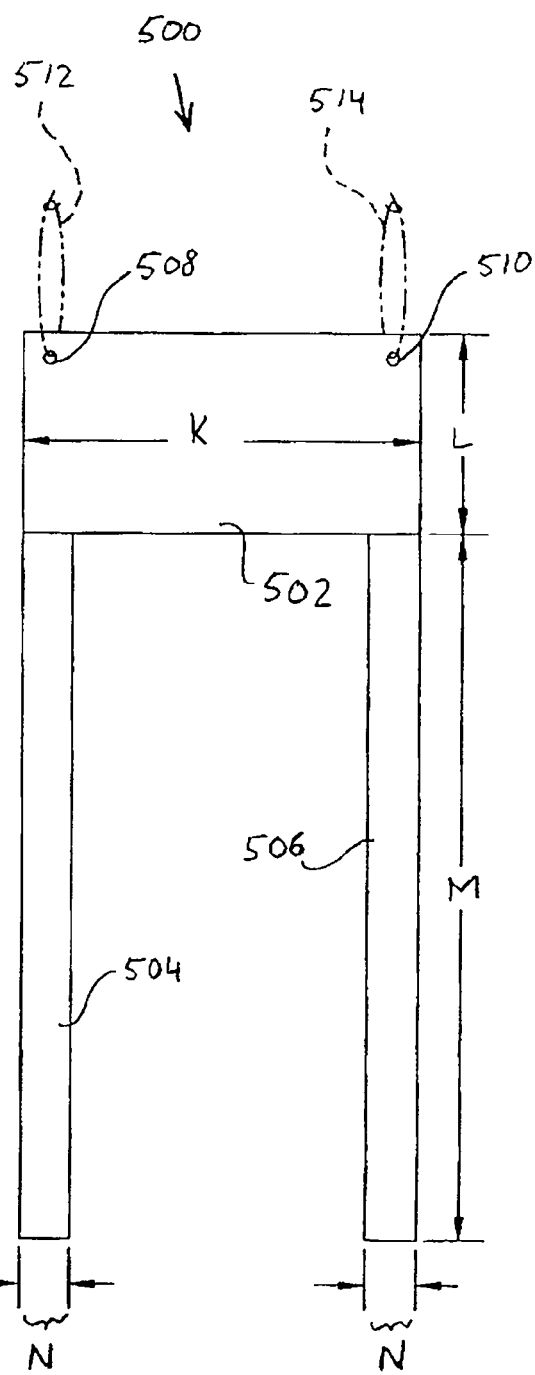
FIG. 5 is a front elevational view of an implant for the treatment of male urinary incontinence as constructed in accordance with another embodiment of the present invention.

Referring now to FIG. 5, there is shown a further embodiment of an implant 500 falling within the scope of the present invention. As depicted, the implant includes a support portion 502 and first and second support portions 504, 506 depending therefrom in generally parallel relation to define an inverted U-shape. The support portion 502 further includes first and second apertures 508, 510 formed thereon through which dedicated sutures 512, 514 extend therethrough. The implant 500 is preferably fashioned such that the support portion 502 has a length "K" of approximately 8 cm and a height "L" of approximately 4 cm. Each respective anchor portion 504 will preferably have a length "M" of approximately 45 cm in length and a width "N" of approximately 1 cm in length. Again, the dimensions of such implant can vary as will be understood by those skilled in the art. Specifically, it should be understood that the specific dimensions provided herein can vary by 50% or substantially greater, and retain its ability for use as an implant.

With respect to the implantation of the implant 500, the same is again performed with the patient assuming lithotomy position. A vertical perineal incision is made in the midline dissecting to expose the bulbar urethra and the descending rami bilaterally leaving the bulbar spongiosis intact. One centimeter suprapubic transverse incisions are made 3 cm laterally to the midline on either side. A suitable introducer is then passed from this "stab wound" and tunneled superficially anterior to the pubic symphysis (not retropubically) that exits through the initial perineal incision. A respective one of the sutures 512 or 514 is attached to the introducer and pulled through the upper "stab" incision. This same procedure is repeated on the respective other side with respective other suture 512 or 514. Respective ones of the sutures 512, 514 are tied down to the rectus fascia in the suprapubic area.

A suitable introducer is then passed from outside in or inside out through the obturator foramen. A suture that is attached to a respective one of the anchor portions 504 or 506 on one side is threaded through such introducer. The introducer is retracted and the suture is pulled until the respective one of the ends of either 504, 506 (depending on which portion is attached) can be grasped. The same procedure is repeated with respect to the other anchor portion 504 or 506 whereby a second introducer is passed from outside in or inside out on the contra-lateral side. Both free ends of anchor portions 504 or 506 will be overlapped and secured. Along these lines, such anchor portions 504, 506 will be tied around the descending rami via a transobturator approach and thus secured to itself via a suture.

In a variation of the embodiment and procedure discussed above with respect to implant 500, it is contemplated that as opposed to the use of apertures 508, 510 with dedicated suture lines 512 and 514 affixed thereto, the implant 500 may utilize thumb tack-like anchors (not shown) in the positions of 508 and 510, respectively. Such embodiment will further preferably include a support portion 502 that has a width "K" of 7 cm as opposed to 8 cm. It should be understood that the specific dimensions provided herein can vary by 50% or substantially greater, and retain its ability for use as an implant.

To implant such embodiment, the patient will assume a lithotomy position and a vertical perineal incision will be made in the midline dissecting to expose the bulbar urethra and descending rami bilaterally leaving the bulbar spongiosis intact. The support portion 502 will be attached via these thumb tacks positioned where apertures 508 and 510 are depicted, respectively, on each side of the upper aspect of the descending rami close to the pubic symphysis.

A suitable introducer is then passed from outside in or inside out through the obturator foramen. A suture that is attached to a respective distal-most end of one of the anchor portions 504 or 506 is threaded through the introducer. The introducer is then retracted and the suture is pulled until the distal-most end of a respective one of one of the anchor portions 504 or 506 can be grasped. This portion of a respective one of the anchor portions is wrapped around the ramus and tied down to the support portion. A second introducer is passed from outside in or inside out on the contra-lateral side and the process is repeated with respect to the respective other anchor portion 504 or 506. The support portion 502 is then tacked down at the upper aspect of the descending rami. The anchor portions 504, 506 are then tied around the descending rami via the transobturator approach and then secured on itself via suture attachment.

Figure 6:
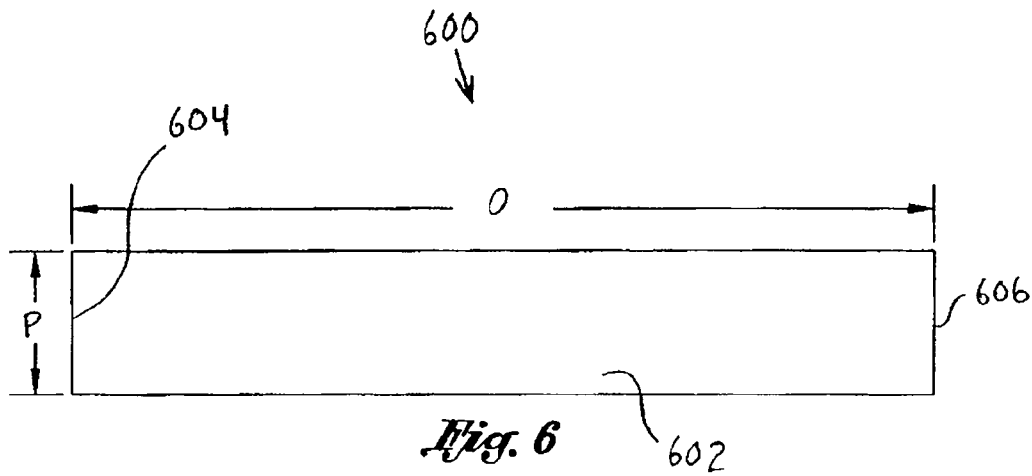
FIG. 6 is a front elevational view of an implant for the treatment of male or female urinary incontinence as constructed in accordance with another embodiment of the present invention.

Referring now to FIG. 6, a further implant 600 is depicted. As illustrated, the implant 600 comprises a generally rectangular implant defining a middle support portion 602 with anchor portions 604, 606 formed integral therewith and defining first and second opposed ends. According to such implant, the same will preferably be formed to have a length "O" of approximately 45 cm and a width "P" of approximately 3 cm. It should be understood that the specific dimensions provided herein can vary by 50% or substantially greater, and retain its ability for use as an implant.

To implant such embodiment 600, a vertical perineal incision is made in the midline dissecting to expose the bulbar urethra and the inferior aspect of the descending rami bilaterally while the patient assumes a lithotomy position. A suitable introducer is passed from outside in or inside out through a 3 cm groin incision that is chosen with the finger in the initial perineal incision to pass through the obturator foramen. A respective end 604 or 606 that is attached to the introducer tip and advanced within the perineal incision. The introducer is retracted through the obturator foramen with the respective other end 604 or 606 being grasped at the lateral groin incision site and cut at skin level. The opposite end 604 or 606 is carried over the bulbar urethral complex. A second suitable introducer is passed from outside in or inside out through another 3 cm groin incision on the contra-lateral side and the process is repeated. The respective ends 604 and 606 of the implant 600 are cut at the level of the skin at the groin incisions.

Figure 7:
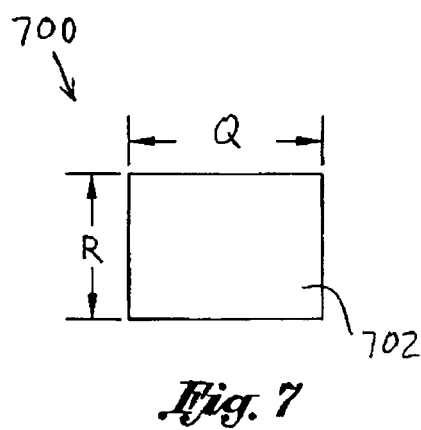
FIG. 7 is a front elevational view of an implant for the treatment of male urinary incontinence as constructed in accordance with another embodiment of the present invention.

The implant in embodiment 700 depicted in FIG. 7 assumes a generally rectangular configuration having a width "Q" of 4 cm and a height "R" of 3 cm. In accordance with the other embodiments, the implant is preferably secured into position by making a vertical perineal incision to the midline dissecting to expose the bulbar urethra and the inferior aspect of the descending rami bilaterally while the patient assumes a lithotomy position. A suture secured on a UR-6 needle is then used to bite into the periosteum of the descending rami bilaterally. Although not shown, there will be four sutures altogether on each side for a total of 8 secured knots to fix the implant 700 into position. The lower three sutures on one side are threaded through the implant, which is placed as high as possible on the bulbar urethral complex. Such lower three sutures are loosely held to stabilize the sling and the top apical suture is then placed, one on each side at the junction of the descending rami to the pubic symphysis. The apical sutures are tied down as tight as possible. The three lower sutures are then tied down accordingly on each side.

Figure 8:
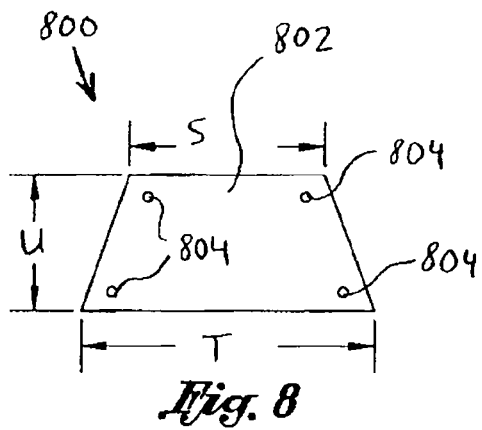
FIG. 8 is a front elevational view of an implant for the treatment of male urinary incontinence as constructed in accordance with another embodiment of the present invention.

In the further embodiment depicted in FIG. 8, the implant 800 assumes a generally trapezoidal having an upper length "S" of approximately 4 cm, a lower length "T" of approximately 6 cm and a height "U" of approximately 3 cm. It should be understood that the specific dimensions provided herein can vary by 50% or substantially greater, and retain its ability for use as an implant. Such implant is secured in position via the initial formation of a vertical perineal incision that is made in the midline dissecting to expose the bulbar urethra and the descending rami bilaterally leaving the bulbar spongiosis intact. The implant 800, which will further preferably have access holes 804 formed thereon, is then placed over the bulbar urethra complex. A fine drill, such as many of a variety well-known to those skilled in the art, is then advanced through each of the holes 804 to secure a preloaded suture. The four sutures that will extend through dedicated ones of the apertures 804 are tied along side of the lateral aspects of the implant 802 to create two knots on each side. The support portion 802 will then be operative to provide the necessary degree of suburethral support.

Figure 9:
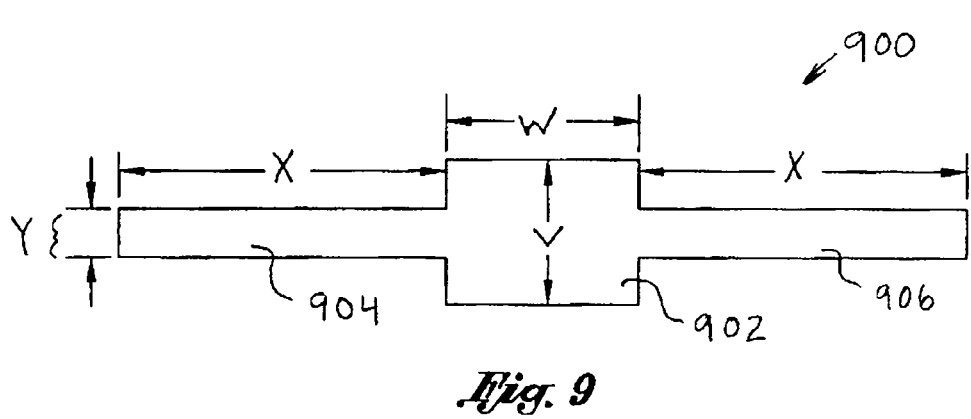
FIG. 9 is a front elevational view of an implant for the treatment of male urinary incontinence as constructed in accordance with another embodiment of the present invention.

In FIG. 9, there is depicted yet a further embodiment of an implant 900 useful in the surgical treatment of male and female urinary incontinence and falling within the scope of the present invention. Such implant will preferably have the dimensions of a height "V" of 3 cm and a width of 4 cm, as the same pertains to the urethral support portion 902. Each anchor portion 904, 906 will preferably have a length "X" of approximately 20 cm and a width "Y" of 1 cm. Along these lines, it should be understood that the specific dimensions provided herein can vary by 50% or substantially greater, and retain its ability for use as an implant. Similar to the embodiment depicted in FIG. 3, such embodiment 900 includes a urethral support portion 902 with two anchor portions 904, 906 extending therefrom in opposed directions. With regard to the best mode by which Applicants would suggest securing such implant 900 into position, such surgical procedure would involve the patient assuming a lithotomy position and, in accordance with the other embodiments discussed above, a vertical perineal incision would be made in the midline dissecting to expose the bulbar urethral and the inferior aspect of the descending rami bilaterally. A suitable introducer would then be passed from inside out or outside in through the upper aspect of the obturator foramen. An end portion of a respective one of the anchor portions 904 or 906 is attached through the introducer. The introducer is retracted and the respective other end of the respective other anchor portion 904 or 906 is grasped and a ratchet closure is done, as will be understood by those skilled in the art. Support portion 902 is carried over the bulbar urethral complex. Thereafter, a second suitable introducer is passed from inside out or outside in on the contra-lateral side and the process repeated with respect to the other respective anchor portion 904, 906. The ends of the sling are then secured to square-like portions of the urethral support portion 902 at the edge of the pubic ramus with a ratchet closure.

Figure 10:
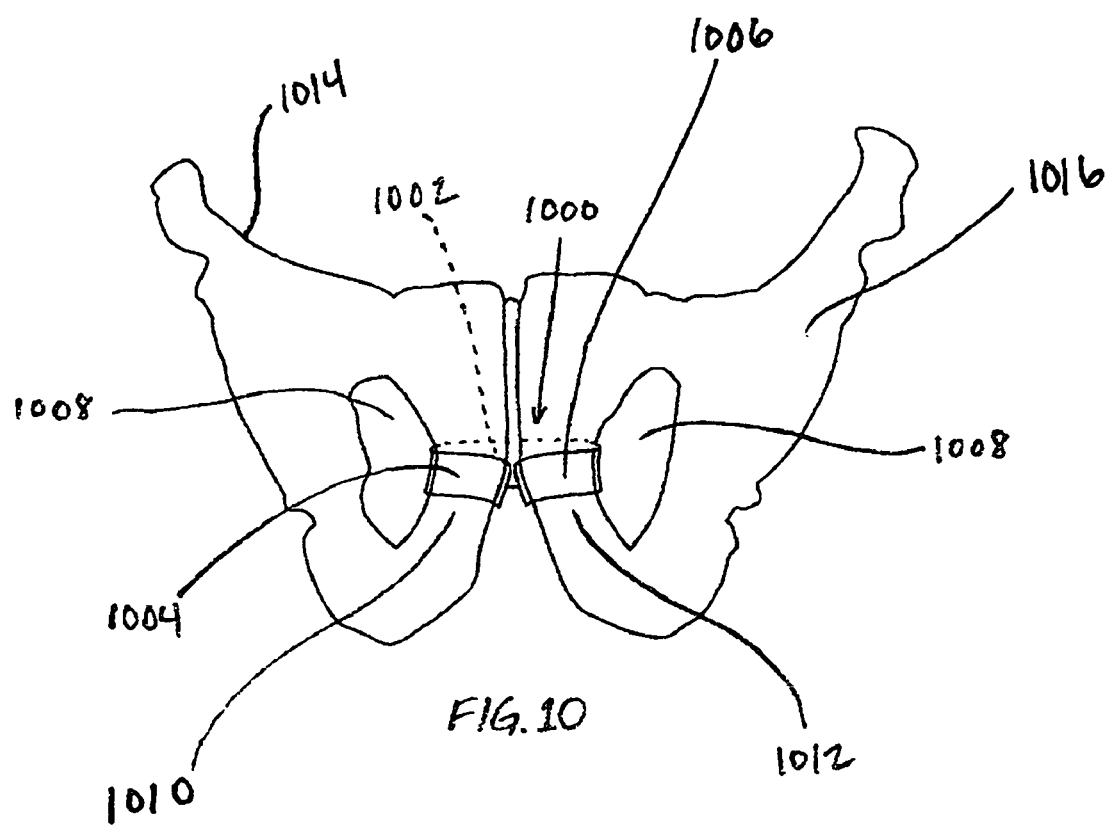
FIG. 10 is a front elevational view of a pelvis, a bladder and a urethra extending therefrom with a sling-type implant shown operatively secured into position, the implant having a support portion aligned at or distal to the bulbar urethra and anchoring portions, the latter shown extending through the obturator foramen and secured about dedicated ones of the rami of each hip bone.
Figure 11:
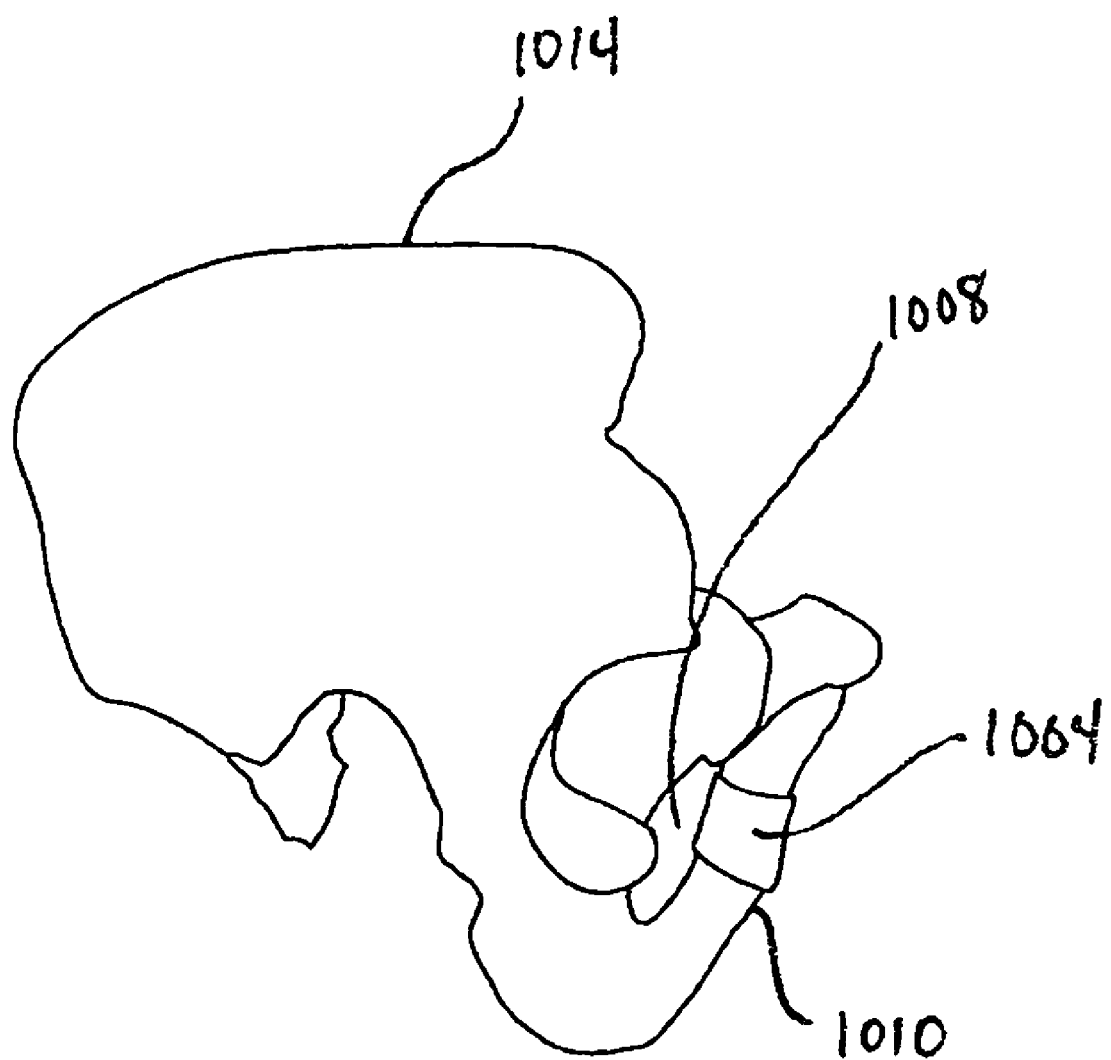
FIG. 11 is a side elevational view of the pelvis and implant of FIG. 10 showing a respective one of the anchor portions of the implant secured about the ramus.

FIGS. 10 and 11 illustrate another embodiment of an implant 1000 positioned in a female patient as contemplated by the present invention. The implant 1000 is situated such that the support portion 1002 thereof is operatively positioned over the urethra. The implant 1000 as depicted includes first and second anchor portions 1004, 1006 that are shown extending through the obturator foramen 1008 and wrapped about dedicated ones of the descending rami 1010, 1012 of hip bones 1014, 1016, respectively.

Figure 12:
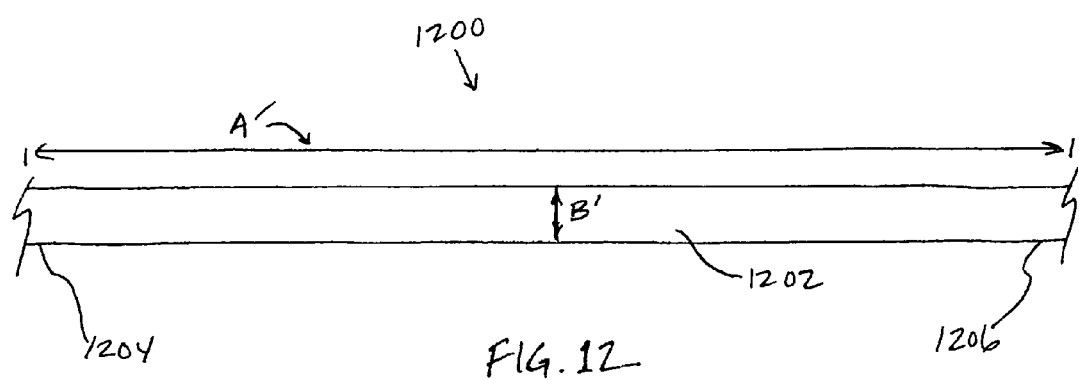
FIG. 12 is a partial front view of an implant for the treatment of urinary incontinence as constructed in accordance with another embodiment of the present invention.
Figure 13:
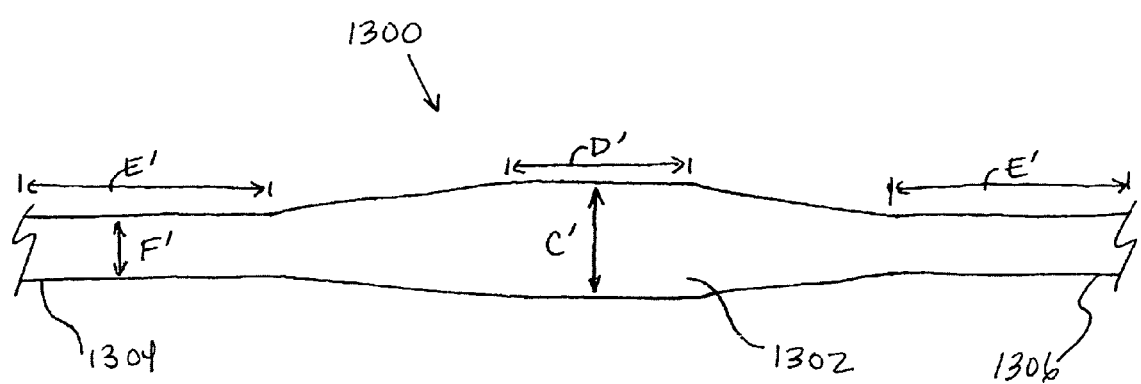
FIG. 13 is a partial front view of an implant for the treatment of urinary incontinence as constructed in accordance with another embodiment of the present invention.

FIGS. 12-13 show additional embodiments of the present invention. FIG. 12 illustrates one embodiment of an implant 1200 comprising a generally rectangular shape defining a middle support portion 1202 with anchor portions 1204, 1206 formed integrally therewith and defining first and second opposed ends. Preferably, the implant 1200 has a length A' of approximately 45 cm and a width B' of approximately 1.1 cm tapering down to 0.6 cm at the lateral ends of the implant. It should be understood that the specific dimensions provided herein can vary by 50% or substantially greater, and retain its ability for use as an implant.

FIG. 13 illustrates another embodiment of the present invention including an implant 1300 defined by a support portion 1302 with anchor portions 1304, 1306 extending in opposing directions therefrom. This embodiment includes a support portion with a width C' of approximately 1.65 cm and a length D' of approximately 2 cm. Anchor portions 1304, 1306 may extend from support portion 1302 via a tapered segment (as shown) and will have a length E' of approximately 20:25 cm and width F' of approximately 1.1 cm. However, one skilled in the art would understand that the specific dimensions provided herein may be modified and still remain within the scope and spirit of the present invention.

Figure 14:
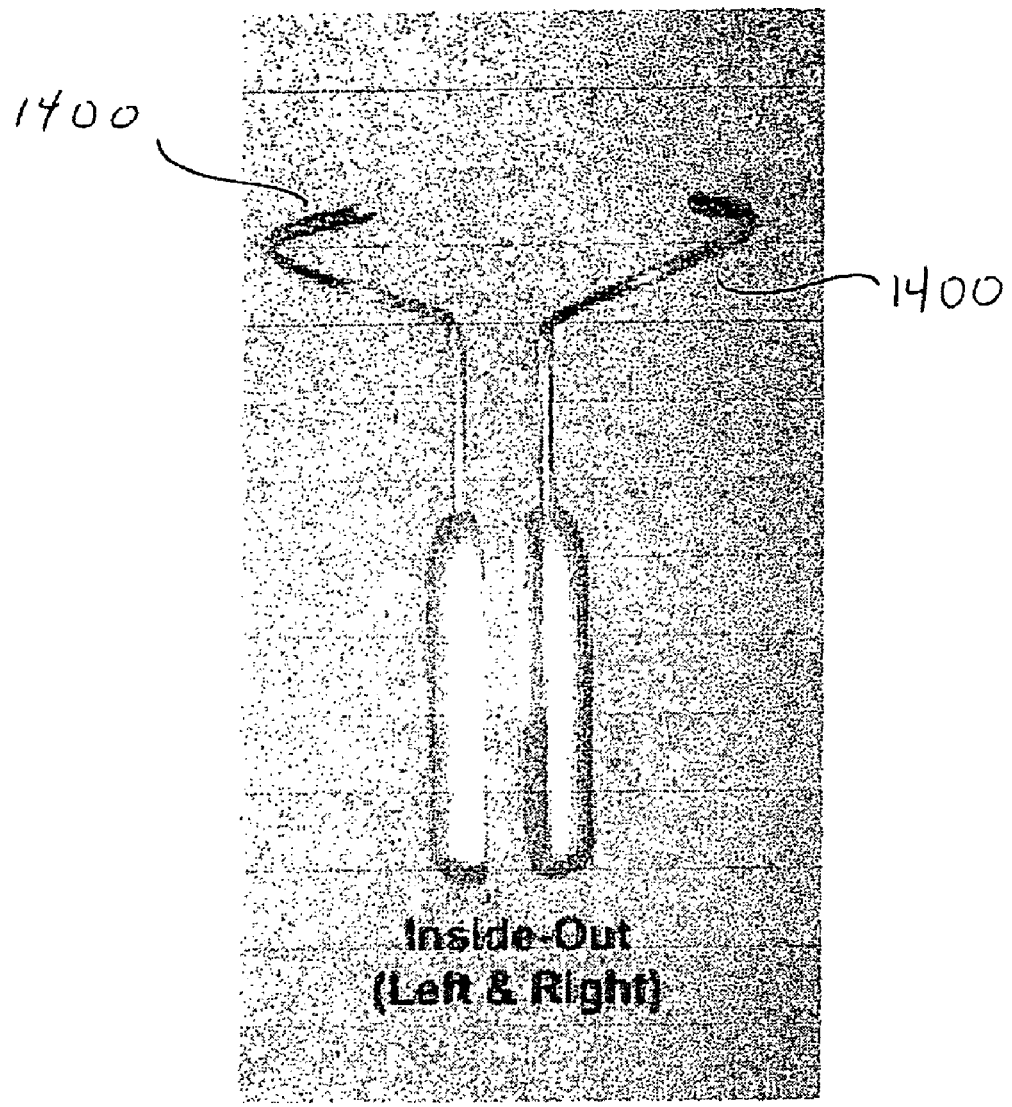
FIG. 14 is a front elevational view of a photograph of an exemplary introducer for use with an implant as contemplated in accordance with the present invention.
Figure 15:
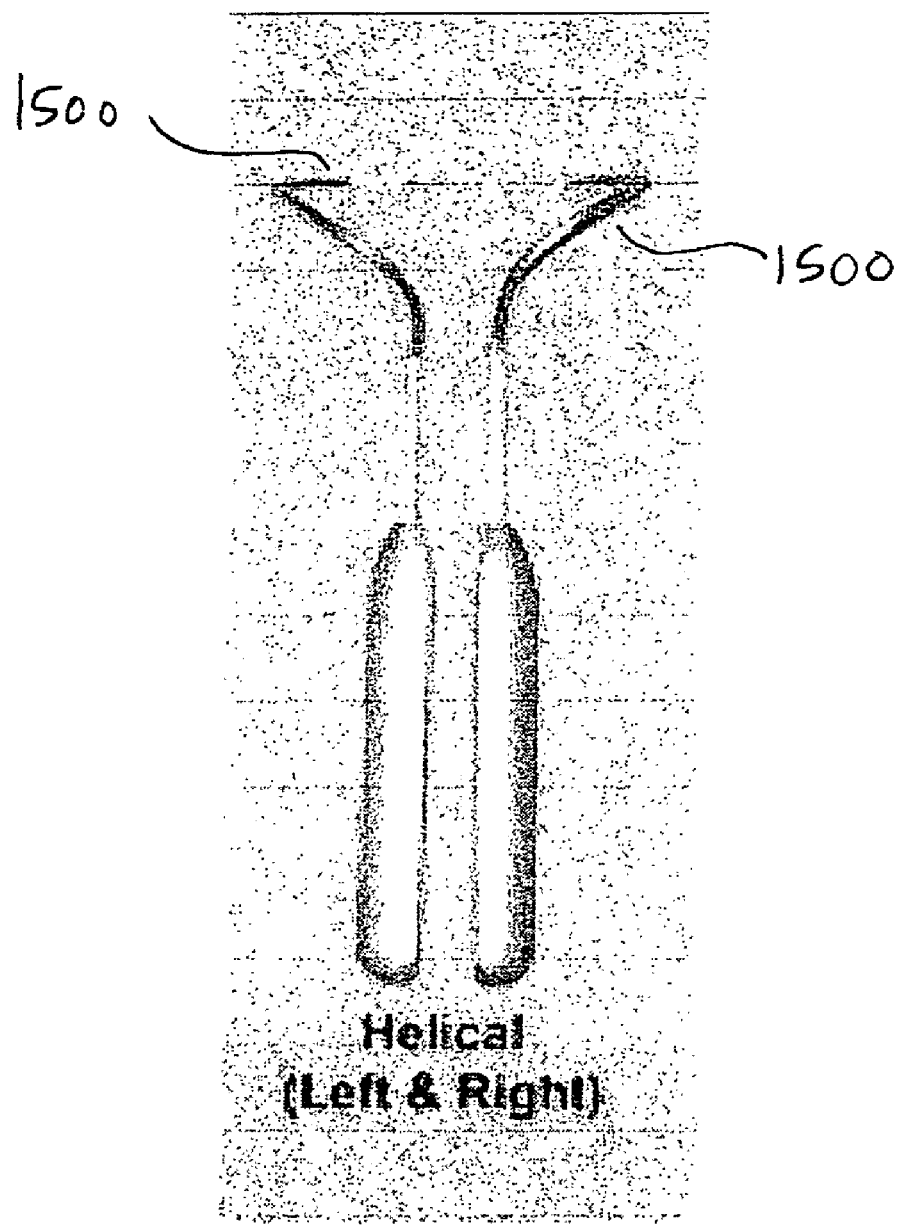
FIG. 15 is a front elevational view of a photograph of an exemplary introducer for use with an implant as contemplated in accordance with the present invention.
Figure 16:
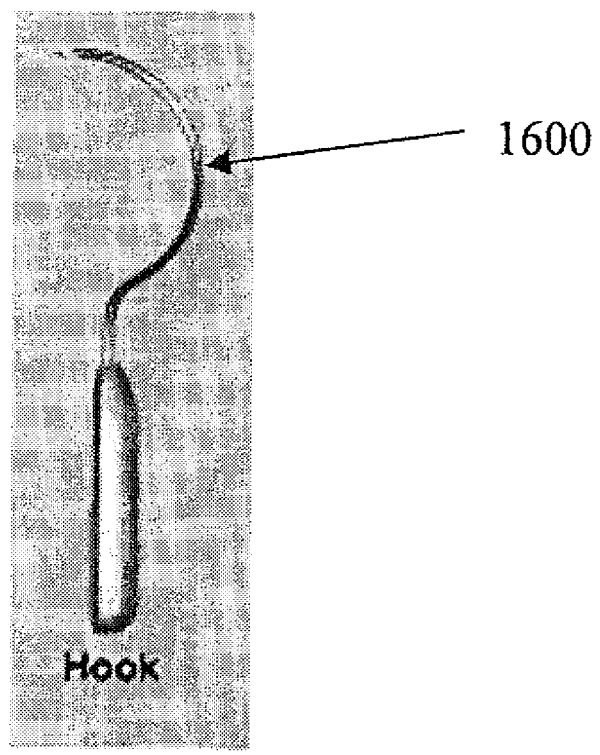
FIG. 16 is a front elevational view of a photograph of an exemplary introducer for use with an implant as contemplated in accordance with the present invention.
Figure 17:
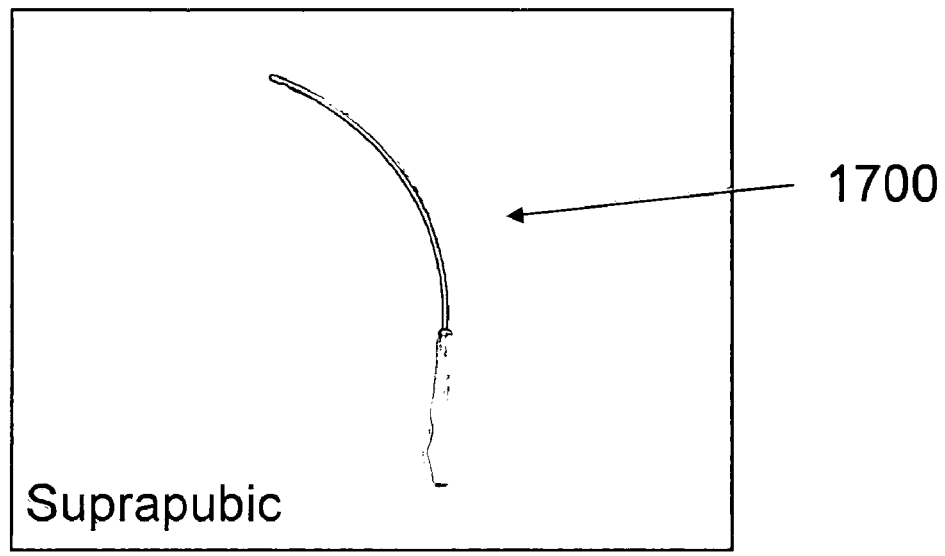
FIG. 17 is a front elevational view of a photograph of an exemplary introducer for use with an implant as contemplated in accordance with the present invention.
Figure 18:
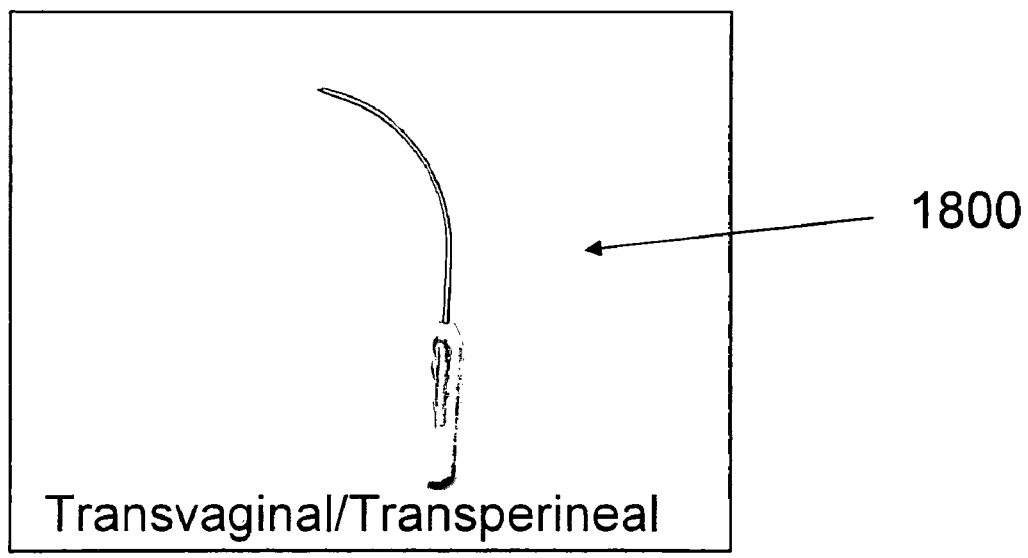
FIG. 18 is a front elevational view of a photograph of an exemplary introducer for use with an implant as contemplated in accordance with the present invention.

Insertion of an implant may be accomplished with various types of suitable introducers, including an inside-out transobturator introducer, a helical transobturator introducer or a hook transobturator introducer as commercially available from the assignee of the present application. FIG. 14 shows an embodiment of a pair of inside-out transobturator introducers 1400, as contemplated herein. FIG. 15 shows an embodiment of a pair of helical transobturator introducers 1500, as contemplated herein. FIG. 16 shows an embodiment of a hook introducer 1600 as contemplated herein. FIG. 17 shows an embodiment of a suprapubic introducer 1700 as contemplated herein. FIG. 18 shows an embodiment of a transvaginal (female)/transperineal (male) introducer 1800 as contemplated herein. One skilled in the art would understand that other similar tools and methods are contemplated herein that could accomplish implantation of the implant as described in the present invention.

The present invention includes methods for placing the implants in a female patient. In one preferred embodiment using an inside-out transobturator introducer (FIG. 14) the method begins with a patient first assuming a lithotomy position then draining the bladder. Next, a midline longitudinal incision is made in the anterior vagina of the patient. Thereafter, on one side of the patient, dissection is performed to expose the inferior and superior surfaces of the urethra and lateral pelvic sidewalls.

Dissection should continue by perforating the obturator membrane with a scissors. If the obturator membrane is not reached after penetration of about 5 cm, however, the dissection path should be re-evaluated.

Next, the physician selects an implant 1000. In this embodiment, a suture loop (not shown) is attached to each of the anchoring portions 1004, 1006 of the implant. The suture loop of one of the anchoring portions 1004 is connected to a slot at the tip of the inside-out transobturator introducer 1400. The inside-out transobturator introducer 1400 is then inserted through the vaginal incision and guided through the obturator foramen around the posterior surface of the ischial pubic ramus. The introducer 1400 is further guided around the anterior surface of the ischial pubic ramus until the tip of the introducer 1400 is exposed in the vaginal dissection.

The suture loop is then removed from the slot of the inside-out transobturator introducer 1400 and the introducer 1400 is removed from the body. The implant 1000 is then pulled through the pathway created by the introducer 1400 until the end of the implant is exposed at the vaginal dissection. Then the physician performs the same steps for the other side of the patient until the ends of the anchoring portions 1004, 1006 of the implant 1000 are now extending through each obturator foramen of the patient and terminating at the vaginal dissection.

Now the physician secures the implant 1000 in the correct position. In this regard, the implant is first aligned mid-urethrally with an appropriate instrument (e.g., a urethral dilator or a curved scissors) placed between the implant 1000 and the urethra to indicate the desired tension to place on the urethra. While maintaining this tension, the suture loops of each anchor portion 1004, 1006 of the implant 1000 are removed and the anchor portions 1004, 1006 are trimmed to the length most suitable for completing the procedure.

To complete the procedure, each end of the anchor portions 1004, 1006 may be connected to the support portion 1002 of the implant 1000 with a suture thus securing the implant 1000 around the ischial pubic ramus. Alternatively, each end of the anchor portions 1004, 1006 may be left loose along the anterior surface of the ischial pubic ramus, the surrounding tissue serving to secure these anchor portions 1004, 1006 in place around the ischial pubic ramus. Finally, any excess vaginal mucosa in the wound is trimmed and the vaginal incision is closed. If desired, vaginal packing coated with estrogen and/or antibiotic ointment may be placed in the wound for a period of time, e.g., 12 hours.

In a second embodiment of a method in accordance with the present invention, a hook (FIG. 16) or a helical (FIG. 15) transobturator introducer is used. In this embodiment, a midline longitudinal incision is first made in the anterior vagina followed by dissection to expose the inferior and superior surfaces of the urethra and the lateral pelvic sidewalls. Blunt finger dissection may be used to develop the existing plain inferior to the endopelvic fascia.

On the patient's thigh region, the physician then palpates the medial border of the obturator foramen in order to locate the base of the adductor longus tendon at the level of the clitoris. At this location, just under the tendon and lateral to the bone, a small incision is made with a scalpel (e.g., a 15 scalpel). The same small incision is made in the corresponding location on the other side of the patient. The physician then takes either a helical or a hook transobturator introducer 1500, 1600 and inserts the introducer through the incision (on one side) and guides the introducer around the posterior surface of the ischial pubic ramus until the tip of the helical or hook introducer appears in the vaginal dissection.

An implant 1000 is then selected. In one embodiment, the anchoring portions 1004, 1006 of the implant 1000 will each have a suture loop (not shown) attached thereto. The suture loop is inserted into a slot at the tip of the introducer 1500 or 1600 and the introducer is then guided back along its previous path around the posterior surface of the ischial pubic ramus back towards the incision made on the patient's abdomen.

Figure 19:
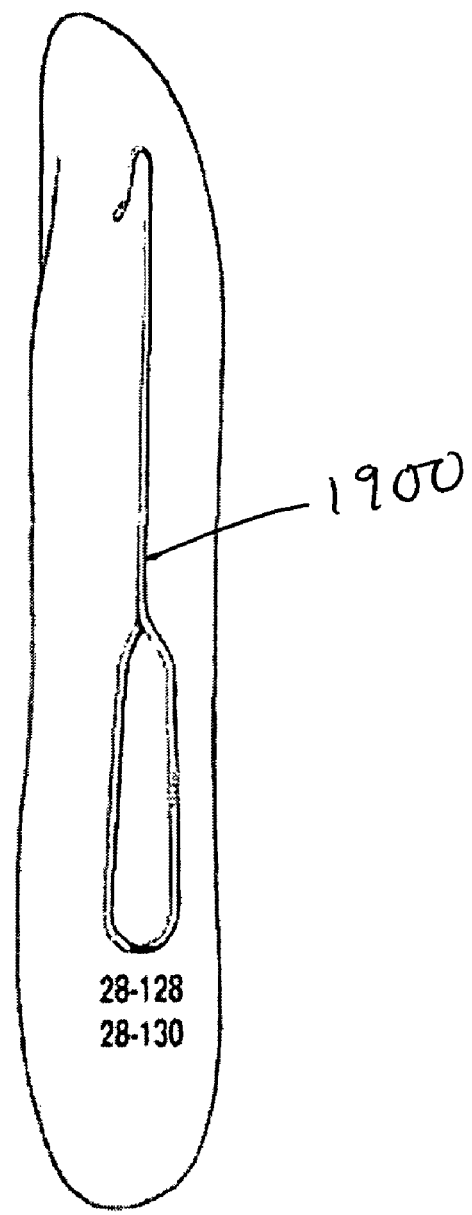
FIG. 19 is a front elevational view of a drawing of an exemplary transvaginal or transperineal tool for use with an implant as contemplated in accordance with the present invention.

The physician then takes a curved tool, such as a Stewart Crypt Hook (FIG. 19), a suprapubic introducer 1700, or a transvaginal introducer 1800 and inserts the curved tool through the vaginal incision and urges the curved tool along the anterior surface of the ischial pubic ramus towards the thigh region incision. The user then uses the curved tool to grab the suture loop from the transobturator introducer. The curved tool is then pulled back towards the vaginal incision pulling the anchoring portion of the implant 1000 towards the vaginal incision until the anchoring portion of the implant is exposed in the vaginal incision. The suture loop is then removed from the tip of the curved tool and the transobturator introducer (either hook 1600 or helical 1500) is removed from the body. The same steps are then performed for the opposite side of the patient until both anchoring portions 1004, 1006 of the implant 1000 are exposed in vaginal incision.

Now the physician secures the implant 1000 in the correct position. In this regard, the implant is first aligned mid-urethrally with an appropriate instrument (e.g., a urethral dilator or a curved scissors) placed between the implant 1000 and the urethra to indicate the desired tension to place on the urethra. While maintaining this tension, the suture loops of each anchor portion 1004, 1006 of the implant 1000 are removed and the anchor portions 1004, 1006 are trimmed to the length most suitable for completing the procedure.

To complete the procedure, each end of the anchor portions 1004, 1006 may be connected to the support portion 1002 of the implant 1000 with a suture thus securing the implant 1000 around the ischial pubic ramus. Alternatively, each end of the anchor portions 1004, 1006 may be left loose along the anterior surface of the ischial pubic ramus, the surrounding tissue serving to secure these anchor portions 1004, 1006 in place around the ischial pubic ramus. Finally, any excess vaginal mucosa in the wound is trimmed and the vaginal incision is closed. The abdominal incisions are also closed, preferably with Steri-strips or Dermabond. If desired, vaginal packing coated with estrogen and/or antibiotic ointment may be placed in the vaginal wound for a period of time, e.g., 12 hours.

Additional general procedure aspects for pre- and post-procedure applications are contemplated herein and further described in Applicant's co-owned and co-pending U.S. patent application Ser. Nos. 10/684,861 and 10/947,182, which are herein incorporated by reference in their entireties.

Although the invention has been described in terms of particular embodiments and applications, one of ordinary skill in the art, in light of the teaching, can generate embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating urinary incontinence, comprising:
    making an incision exposing urethral tissue in a patient;

inserting an implant into said urethral incision;

suspending the implant between a first obturator foramen and a second obturator foramen of the patient and elevating a urethra of the patient with a center portion of said implant by extending one end of said implant through the first obturator foramen of said patient and securing said one end of said implant around a first ischial pubic ramus of said patient and extending an opposite end of said implant through the second obturator foramen of said patient and securing said opposite end of said implant around a second ischial pubic ramus of said patient.

2. A method as set forth in claim 1, wherein said incision is a perineal incision.

3. A method as set forth in claim 1, wherein said incision is a vaginal incision.

4. A method as set forth in claim 1, wherein suspending the implant between a first obturator foramen and a second obturator foramen of the patient comprises:

attaching said one end of said implant to a tip of an inside-out transobturator tool; and, urging said inside-out transobturator tool through said first obturator foramen and back towards said incision.

5. The method of claim 1, wherein suspending the implant between a first obturator foramen and a second obturator foramen of the patient comprises wrapping said one end and said opposite end of said implant around a respective one of said first ischial pubic ramus and said second ischial pubic ramus on either side of said patient.

6. A method of treating urinary incontinence by supporting a urethra of a patient, the comprising:

forming an incision and exposing urethral tissue in a patient;

inserting an implant into the incision;

elevating the urethra of the patient with a support portion of the implant; and suspending the support portion of the implant between a first end portion of the implant that is secured around a first ischial pubic ramus of the patient and a second end portion of the implant that is secured around a second ischial pubic ramus of the patient.

7. The method of claim 6, comprising extending the first end portion of the implant through a first obturator foramen of the patient and extending the second end portion of the implant, through a second obturator foramen of the patient.

8. A method of treating urinary incontinence by supporting a of a patient, the comprising:

forming an incision and exposing tissue around the urethral of the patient;

inserting an implant into the incision; and securing a first end portion of the implant around a first ischial pubic ramus of the patient and securing an opposing second end portion of the implant around a second ischial pubic ramus of the patient, suspending the implant between a first obturator foramen and a second obturator foramen of the patient, and elevating the urethra of the patient with a centrally located support portion of the implant.

9. The method of claim 8, wherein forming an incision and exposing tissue around the urethral of the patient comprises forming a single incision in the patient and dissecting tissue around the urethral of the patient, and inserting an implant into the incision comprises inserting an implant into the single incision.

* * * * *